United States Patent
Heinecke (10) Patent No.: US 6,939,716 B2
(45) Date of Patent: Sep. 6, 2005

(54) METHOD FOR DETECTING CONDITIONS INDICATIVE OF SEPSIS

(75) Inventor: Jay W. Heinecke, Seattle, WA (US)

(73) Assignee: Washington University, St. Louis, MO (US)

( * ) Notice: Subject to any disclaimer, the term of this patent is extended or adjusted under 35 U.S.C. 154(b) by 324 days.

(21) Appl. No.: 10/225,700

(22) Filed: Aug. 22, 2002

(65) Prior Publication Data

US 2003/0100122 A1 May 29, 2003

Related U.S. Application Data

(60) Provisional application No. 60/323,532, filed on Sep. 19, 2001.

(51) Int. Cl.⁷ .............................................. G01N 33/00
(52) U.S. Cl. .................... 436/89; 436/173; 436/811; 435/7.1; 435/7.92; 435/40.52; 435/69.6
(58) Field of Search ............................ 436/811, 89, 173, 436/501, 518; 435/7.1, 7.92, 40.52, 69.6

(56) References Cited

U.S. PATENT DOCUMENTS

| | | | |
|---|---|---|---|
| 5,639,617 A | * 6/1997 | Bohuon ...................... | 435/7.1 |
| 5,731,208 A | 3/1998 | Heinecke ...................... | 436/86 |
| 6,096,556 A | 8/2000 | Heinecke ...................... | 436/89 |
| 6,133,039 A | 10/2000 | Heinecke ...................... | 436/89 |
| 6,268,220 B1 | * 7/2001 | Heinecke .................... | 436/501 |
| 6,306,576 B1 | * 10/2001 | Hazen et al. ................... | 435/4 |

FOREIGN PATENT DOCUMENTS

| | | | | |
|---|---|---|---|---|
| WO | WO 93/24143 | 12/1993 | .......... | A61K/37/64 |
| WO | WO 93/25230 | 12/1993 | .......... | A61K/37/64 |
| WO | WO 00/49411 | * 8/2000 | .......... | G01N/33/55 |
| WO | WO 01/63280 | * 8/2001 | .......... | G01N/33/53 |

OTHER PUBLICATIONS

Bernard et al., *New Engl. J. Med.*, 344, 699–709 (2001).
Henderson et al., *J. Biol. Chem.* 276, 7867–7875 (2001).
Brennan et al., *J. Clin. Invest.* 107, 419–430 (2001).
Hotchkiss et al., *Crit. Care Med.* 25, 1298–1307 (1997).
Freeman et al., *Crit. Care Med.* 28, 1701–1708 (2000).
Cobb et al., *Surgery*, 126, 438–442 (1999).
Anon., *Gen. Engr. News*, May 1, 1999, pp 7, 51,57 Article on "Sepsis Therapy Remains Elusive".
Winterboum, Christine C. and Kettle, Anthony J. Free Radical Biol. & Med. vol. 29, No. 5, pp. 403–409 (2000).
Gaut, Joseph P. et al., Proc. Natl. Acad. Sci. USA, vol. 98, No. 21, pp. 11961–11966 (2001).

* cited by examiner

*Primary Examiner*—Monique T. Cole
(74) *Attorney, Agent, or Firm*—Harness, Dickey & Pierce P.L.C.

(57) ABSTRACT

The disclosure describes a method for detecting conditions indicative of sepsis. In one embodiment of the invention, an increase in the level of 3-chlorotyrosine or 3-bromotyrosine from the normal level in a sample of body fluid or tissue is indicative of early sepsis or infection. In another embodiment of the invention, the level of 3-chlorotyrosine or 3-bromotyrosine is measured or monitored to determine the response to therapeutic treatment of the infective condition in which a reduction in the level that existed prior to the treatment is an early sign or indication that the treatment is working in vivo. In a preferred embodiment, the method of the invention is illustrated in a clinically relevant mouse model of sepsis.

7 Claims, 6 Drawing Sheets

METHOD FOR DETECTING CONDITIONS INDICATIVE OF SEPSIS

This application claims the benefit of application Ser. No. 60/323,532, filed Sep. 19, 2001.

This invention was made in part with government support under grant number AG12293, awarded by the National Institutes of Health. The government has certain rights in the invention.

FIELD OF THE INVENTION

The present invention relates to the field of detecting conditions indicative of sepsis.

BACKGROUND OF THE INVENTION

Sepsis is a toxic condition resulting from the spread of bacteria or their products from a focus of infection, especially septicemia. According to the Centers for Disease Control (CDC), septicemia is a leading cause of death in the United States, especially among the elderly. Death can occur in 40% to 60% of the patients with septicemia. It has been estimated that some five hundred thousand cases of sepsis occur annually in the United States. Accordingly, methods for detecting conditions indicative of sepsis would have significant use in medical practice.

Currently, sepsis remains an elusive therapeutic target. Pharmaceutical companies have developed potential therapeutics for action against sepsis-causing bacterial components and against chemical signaling molecules in inflammatory and coagulation pathways. Agents such as monoclonal antibodies and antagonists of tumor necrosis factor (TNF) have been developed for treatment of sepsis, but not with great success. Scavengers of nitric oxide (NO) have also been proposed since nitric oxide has been implicated as a mediator in the inflammatory cascade that leads to shock. Coagulation pathway molecules such as LACI or TFPI have been developed for treatment of sepsis and septic shock as disclosed, e.g., in PCT International Applications WO 93/241,143, published Dec. 9, 1993, and WO 93/252,230, published Dec. 23, 1993. Most recently a human-activated protein C, which is a vitamin K dependent protein of blood plasma, has been produced by recombinant DNA and reported to be clinically studied with effective results against sepsis, Bernard et al., *New England Journal of Medicine*, Vol. 344, pp. 699–709, March 2001. The latter drug has been designated with the name "Xigris."

For treatment of sepsis, good identifying or diagnostic markers to predict which patients can benefit from therapy and to monitor the response to treatment during infection are in great need.

Oxidants are thought to be key components of the neutrophil host defense system (ref. 1). Upon contact with a pathogen, neutrophils produce a respiratory burst characterized by intense uptake of oxygen. The resulting superoxide dismutates into hydrogen peroxide ($H_2O_2$) (ref. 2). The toxicity of $H_2O_2$ is greatly enhanced by the heme enzyme myeloperoxidase, which uses $H_2O_2$ to convert chloride ($Cl^-$) into hypochlorous acid (HOCl) (refs. 3–8).

$$Cl^- + H_2O_2 + H^+ \rightarrow HOCl + H_2O$$

Remarkably, myeloperoxidase is the only mammalian enzyme known to oxidize $Cl^-$ to HOCl at plasma concentrations of halide (refs. 3–6).

Chloride is considered the major halide used by myeloperoxidase. Bromide ($Br^-$) has attracted little attention because its extracellular concentration is at least 1,000-fold lower than that of $Cl^-$ (plasma [$Cl^-$] 100 mM, plasma [$Br^-$] 20-100 $\mu$M) (ref. 9). However, brominating intermediates such as HOBr are also potent antimicrobial oxidants in vitro (refs. 10,11).

It has been recently demonstrated that myeloperoxidase can both chlorinate and brominate nucleobases at plasma levels of halide (ref. 12). In the reaction pathway, myeloperoxidase initially produces HOCl, which reacts with $Br^-$ to generate brominating intermediates (ref. 12). It has not been established heretofore whether this brominating pathway is physiologically relevant.

It also has not been known heretofore whether the myeloperoxidase system is cytotoxic to bacteria in vivo, though myeloperoxidase-deficient mice are susceptible to fungal infection (refs. 13,14).

BRIEF DESCRIPTIONS OF THE INVENTION

In accordance with the present invention a method is provided for detecting conditions indicative of sepsis.

In one embodiment of the invention, an increase in the level of 3-chlorotyrosine or 3-bromotyrosine from the normal level in a sample of body fluid or tissue is indicative of early infection or sepsis. The elevated level of 3-chlorotyrosine or 3-bromotyrosine can serve as a diagnostic marker for early infection or sepsis.

In another embodiment of the invention, the level of 3-chlorotyrosine or 3-bromotyrosine is measured or monitored to determine the response to treatment of the infective condition, e.g., treatment with antibiotic or other such therapy. A reduction in the level that existed prior to treatment is an early sign or indication that the treatment is working in vivo.

In order to illustrate the effectiveness of the invention, the role of the myeloperoxidase system in host defense against invading bacteria was tested in a clinically relevant mouse model of sepsis (refs. 15–18) and gas chromatography/mass spectrometry (GC/MS). This mouse model of polymicrobial sepsis showed that the myeloperoxidase system generated antimicrobial brominating and chlorinating intermediates in vivo that could be determined by measuring the level of 3-chlorotyrosine or 3-bromotyrosine in a sample of peritoneal fluid.

The myeloperoxidase system of neutrophils uses hydrogen peroxide and chloride to generate hypochlorous acid, a potent bactericidal oxidant in vitro. In the stated mouse model of polymicrobial sepsis, it was observed that mice deficient in myeloperoxidase were more likely than wild-type mice to die from infection. Mass spectrometric analysis of peritoneal inflammatory fluid from septic wild-type mice detected elevated concentrations of 3-chlorotyrosine, a characteristic end product of the myeloperoxidase system. Levels of 3-chorotyrosine did not rise in the septic myeloperoxidase-deficient mice. Thus, myeloperoxidase appears to protect against sepsis in vivo by producing halogenating species.

More surprisingly, it was found that levels of 3-bromotyrosine were also elevated in peritoneal fluid from septic wild-type mice, and were markedly reduced in peritoneal fluid from septic myeloperoxidase-deficient mice. Furthermore, physiologic concentrations of bromide modulated the bactericidal effects of myeloperoxidase in vitro. It appears, therefore, that myeloperoxidase can use bromide as well as chloride to produce oxidants in vivo, even though the extracellular concentration of bromide is at least 1,000-fold lower than that of chloride. Thus, myeloperoxidase plays an important role in host defense against bacterial pathogens, and bromide is believed to be a previously unexpected component of this system.

Although the present inventor in U.S. Pat. No. 6,268,220 previously described the presence of elevated levels of 3-chlorotyrosine in body tissue as a diagnostic marker for atherosclerosis, the present invention is directed to an entirely different class or group of patients. On the one hand, the patient being evaluated for atherosclerosis would normally be a patient who had experienced pain of angina pectoris, emotional stress, or other such cardiovascular conditions and symptoms. On the other hand, the patient to which the method of the present invention is directed is a patient that may be susceptible to infection or already is thought to possibly have an infection.

DETAILED DESCRIPTION OF THE INVENTION

While the specification concludes with claims particularly pointing out and distinctly claiming the subject matter regarded as forming the invention, it is believed that the invention will be better understood from the following preferred embodiments of the invention taken in conjunction with the accompanying drawings.

BRIEF DESCRIPTION OF THE DRAWINGS

FIG. 3 shows Isotope dilution GC/MS quantification of A, 3-chlorotyrosine (3-Cl-Tyr) and B, 3-bromotyrosine (3-Br-Tyr) in the peritoneal inflammatory fluid of sham-operated and CLP-subjected mice. Oxidation products were monitored in myeloperoxidase-deficient ($MPO^{-/-}$) mice, and in wild-type (WT) mice in the 129/SvJ and C57BL/6J background.

FIG. 5 is a graphical showing of reaction requirements for the generation of N-acetyl-L-3-bromotyrosine by phagocyte peroxidases and hypohalous acids at neutral pH. Reactions were carried out in buffer A supplemented with 10 $\mu$M $Br^-$ A, shows effect of pH on the generation of N-acetyl-bromotyrosine by myeloperoxidase.

B–E, shows effect of taurine (200 $\mu$M) on the generation of N-acetyl-bromotyrosine by, respectively, HOCl, HOBr, myeloperoxidase or eosinophil peroxidase at pH 7.

Amino acids were quantified by reverse-phase HPLC. Results are representative of those found in three independent experiments. MPO, myeloperoxidase; EPO, eosinophil peroxidase; Ac, acetyl.

FIG. 6 is a graphical showing of reaction requirements for the generation of N-acetyl-L-3-chlorotyrosine and N-acetyl-L-3-bromotyrosine by phagocyte peroxidases and hypohalous acids under acidic conditions. Effect of [$Br^-$] on the generation of N-acetyl-chlorotyrosine and N-acetyl-bromotyrosine by:

A, HOCl; or

B, myeloperoxidase.

Effect of taurine on the generation of N-acetyl chlorotyrosine and N-acetyl-bromotyrosine by:

C, hypohalous acid (HOCl, HOBr); or

D, phagocyte peroxidases (MPO, EPO).

Reactions for A and B were carried out as described in the description of FIG. 4. Reactions for C and D were performed as described in the description of FIG. 4 except the pH was 5.9. Amino acids were quantified by reverse-phase HPLC. Results are representative of those found in 3 independent experiments. MPO, myelo-peroxidase; EPO, eosinophil peroxidase; Ac, acetyl.

In order to illustrate the invention in greater detail, the following specific laboratory examples were carried out. Although specific examples are thus illustrated herein, it will be appreciated that the invention is not limited to these specific, illustrative examples or the details therein.

EXAMPLES

Materials. All materials were purchased from Sigma-Aldrich (St. Louis, Mo.) or Fisher (Pittsburgh, Pa.) unless otherwise indicated. Isotope-labeled amino acids were from Cambridge Isotope Laboratories (Andover, Mass.). Rabbit polyclonal antibody was raised against a peptide present in mouse myeloperoxidase (NTLPKLNLTSWKET) [SEQ ID NO:1] (ref. 14).

Animals. The Animal Studies Committee of Washington University School of Medicine approved all animal studies. Myeloperoxidase-deficient mice were generated in a 129/SvJ background; they were backcrossed at least 4 generations into the C57BL/6J background prior to use (ref. 14). C57B1/6J and Sv129/J mice were from Jackson Laboratories (Bar Harbor, Mass.). Mice were maintained under pathogen-free conditions on a 12 h light-dark schedule and allowed ad lithium access to rodent diet 5001 (Harlan-Teklad, Madison, Wis.).

General procedures. Myeloperoxidase was purified from HL60 cells (ref. 19). Enzyme was apparently pure as assessed by its absorption spectrum ($A_{430}/A_{280}$ ratio>0.8), SDS-PAGE, and peroxidase activity gel electrophoresis (ref. 20). Porcine eosinophil peroxidase ($A_{415}/A_{280}$>0.9) was from ExOxEmis (Little Rock, Ark.). Chloride-free NaOCl and HOBr were prepared by conventional procedures as described previously (refs. 21,22). Peritoneal white blood cells were elicited with intraperitoneal (i.p.) injection of 4% thioglycollate and harvested 24 h after injection (ref. 23). SDS-PAGE was performed using 10% Bis-Tris NuPAGE gels (Invitrogen; Carlsbad, Calif.). The separated proteins were transferred onto a nitrocellulose membrane, which was blocked overnight at 4° C. with 5% milk and 0.05% Tween-20 in phosphate-buffered saline (PBS; 10 mM phosphate, 138 mM NaCl, 2.7 mM KCl, pH 7.4). The blot was then incubated (1 h) with rabbit anti-mouse myeloperoxidase antibody (1:1,000) followed by goat anti-rabbit immunoglobulin antibody (1:10,000; Santa Cruz Biotechnology; Santa Cruz, Calif.) conjugated with horseradish peroxidase. West Pico chemiluminescent substrate (Pierce; Rockford, Ill.) was added, and the membrane was exposed to autoradiography film and developed.

Reaction conditions. Reactions were carried out for 60 min at 37° C. in buffer A (100 mM NaCl, 50 mM sodium phosphate, 100 µM diethylenetriaminepentaacetic acid (DTPA)) supplemented with 1 mM N-acetyl-L-tyrosine and either 50 µM hypohalous acid or 3 nM peroxidase and 50 µM $H_2O_2$. Buffer A was passed over a Chelex resin column prior to use to remove redox active transition metal ions. Reactions were initiated by the addition of oxidant and terminated with 0.1 mM methionine.

Reverse-phase HPLC analyses of halogenated amino acids. Analyses were performed using a flow rate of 1 mL/min and an Ultrasphere ODS reverse-phase column (4.6 mm×25 cm; 5 µm; Beckman Instruments; Berkeley, Calif.) coupled to a Waters 484 Tunable Absorbance Detector with monitoring at 275 nm. Solvent A was 0.1% trifluoroacetic acid (TFA, pH 2.5), and solvent B was 0.1% TFA in methanol (pH 2.5). The gradient profile was: isocratic elution at 66:34 (v/v) A:B over 2.1 min; linear increase of B from 34% to 40% over 30 min; isocratic elution at 60:40 A:B for 3 min; increase of B from 40% to 100% over 2 min; and isocratic elution at 100% B for 3 min. Products were quantified using integrated peak areas by comparison to standard curves of authentic N-Ac-chlorotyrosine and N-Ac-bromotyrosine.

Sepsis model. Cecal ligation and puncture of age-matched (8-16 weeks) and sex-matched mice was performed by conventional procedure as previously described (ref. 16). The peritoneum was lavaged 24 h after surgery with 5 mL of PBS or with PBS supplemented with 50 µM butylated hydroxytoluene, 100 µM DTPA, 1 mM sodium azide, and 10 mM aminotriazole. Lavage fluid was stored at –80° C. until analysis. Control experiments demonstrated that inclusion of antioxidants had no effect on the amount of products detected. For survival studies, animals were given i.p. injections of metrinodizole (35 mg/kg) and ceftriazone (50 mg/kg) approximately 1 h after surgery. Antibiotic injections were repeated once 24 h after surgery. Mice were allowed ad libitum access to water and food.

Cell analysis. Cells were pelleted onto slides by centrifugation and stained with a modified Wright's stain (Dimscio & Associates; Manchester, Mo.). Cell counts were performed by the Department of Comparative Medicine (Washington University School of Medicine).

Peroxidase activity assay. Peritoneal lavage fluid was centrifuged at 4° C. for 10 min at 16,000×g. Cetyltrimethylammonium bromide buffer (0.3%; 500 µL) containing 25% glycerol and 35 mM β-alanine (pH 4.5) was added to the pellet, and the mixture was sonicated for 10 min. After a second 10 min centrifugation at 16,000×g, soluble proteins in the supernatant were subjected to native PAGE and peroxidase activity staining (ref. 20).

GC/MS analysis. Isotope-labeled internal standards (1 pmol L-3-chloro[$^{13}C_6$]tyrosine, 500 fmol L-3-bromo[$^{13}C_6$]tyrosine, 10 nmol L-[$^{13}C_9$, $^{15}N$]tyrosine) were added to 500 µL of peritoneal fluid and prepared for GC/MS analysis by conventional procedure as previously described (refs. 24, 25). Briefly, amino acids were isolated using solid-phase extraction with a C18 column followed by a Supelco Chrom P column (refs. 24, 25). Samples were dried under anhydrous $N_2$ and stored at –20° C. until analysis.

Following derivatization with ethyl heptafluorobutyrate and N-methyl-N-(t-butyldimethylsilyl)-trifluoroacetamide+ 1% trimethylchlorosilane (MtBSTFA), the samples were dried under anhydrous $N_2$ and resuspended in 50 µL of undecane/MtBSTFA (3:1 v/v). A 1 µL sample was analyzed by selected ion monitoring using a Hewlett-Packard (HP) 6890 Gas Chromatograph coupled to a HP 5973 Mass Detector in the electron capture negative chemical ionization (EC-NCI) mode. The injector, transfer line, and source temperatures were initially set at 183° C, 300° C., and 250° C., respectively. The injector and transfer line temperatures were set to increase incrementally with the temperature gradient (180° C. to 300° C. at 40° C./min.). 3-Chlorotyrosine and 3-bromotyrosine were quantified using the respective ions at m/z 489 ([M—halide—t-butyl-dimethylsilyl]$^-$) and their isotopically ring-labeled [$^{13}C_6$]-internal standards (m/z 495). Potential artifact formation during sample work-up was monitored as the appearance of ions at m/z 499 derived from L-[$^{13}C_9$, $^{15}N$]tyrosine (refs. 24, 25).

Liquid chromatography-electrospray ionization-MS. N-Acetyl amino acids were separated by reverse-phase HPLC and analyzed with a Finnigan LCQ (ref. 26). Full mass scanning (m/z 100-350) and tandem MS analyses were performed in the negative ionization mode.

Bacterial killing. The bactericidal activity of myeloperoxidase was quantified by conventional procedures as described previously (ref. 27). Briefly, *Klebsiella pneumoniae* were cultured in Luria-Bertani broth to mid-log growth phase, washed with PBS, and used at $10^9$ bacteria/mL. Bacteria were incubated with 5 nM enzyme, 5 nM $H_2O_2$, and 100 mM NaCl in PBS (pH 5.5) for 15 min at 37° C. Serial dilutions were immediately spread on agar plates and the colony forming units determined after overnight incubation at 37° C.

Statistical analysis. The survival study was evaluated using a Fisher's exact P test. All other data were analyzed with a Student's t test. Significance was accepted at $P<0.05$.

RESULTS

Figure 1:
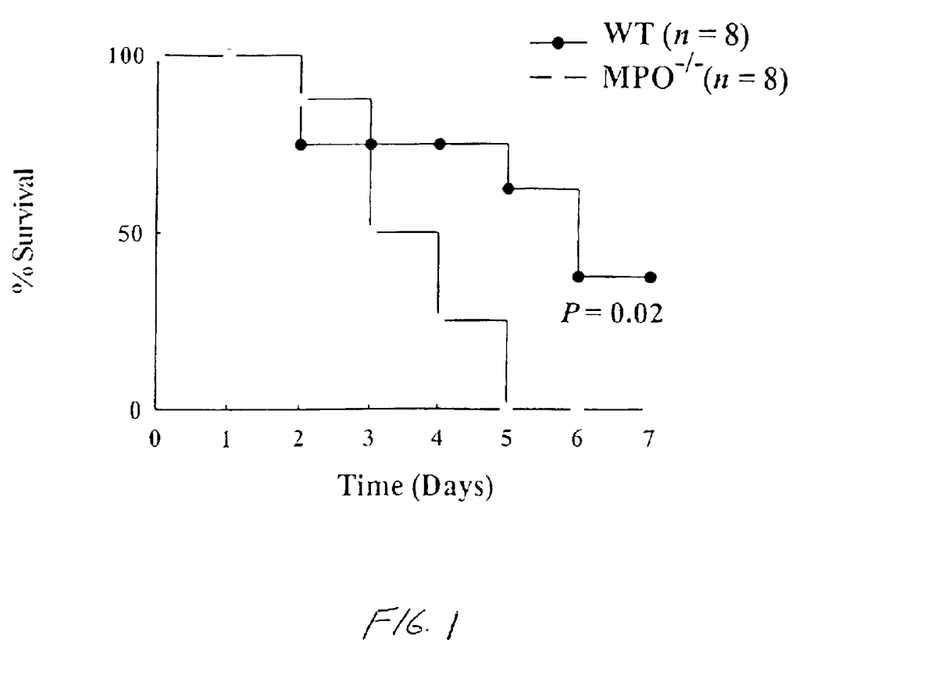
FIG. 1 is a graphical showing that myeloperoxidase deficiency impairs survival in a cecal ligation and puncture (CLP) model of sepsis in which percent of survival is plotted against time in days. Mortality was monitored in myeloperoxidase-deficient ($MPO^{-/-}$) mice and littermate wild-type (WT) controls.

Myeloperoxidase deficiency increases mortality in the cecal ligation and puncture (CLP) model of sepsis. To evaluate the potential role of the myeloperoxidase system in host defense, myeloperoxidase-deficient mice and a clinically relevant and widely utilized model of intra-abdominal infection and sepsis were used. In the cecal ligation and puncture (CLP) model, the blind-ended cecum is ligated and punctured (ref. 16), releasing intestinal microflora into the abdominal cavity. Previous studies have demonstrated that 35–45% of wild-type mice survive this procedure for longer than 7 days (refs. 16, 18). When myeloperoxidase-deficient mice were subjected to CLP, none of the animals were alive five (5) days after surgery (FIG. 1). In contrast, 63% of the wild-type littermate control mice were alive after five (5) days, and 38% were alive after 1 week (FIG. 1; P=0.02).

Neutrophils predominated in the cell populations elicited from both the wild-type mice (n=7; 77±3% neutrophils, 23±3% macrophages, 0.3±0.2% eosinophils) and the myeloperoxidase-deficient mice (n=11; 77±4% neutrophils, 23±3% macrophages, 0.9±0.5% eosinophils). Red blood cells, cellular debris and microorganisms were also apparent in the peritoneal fluid after the mice were subjected to CLP. Importantly, the cellular response to sepsis of the myeloperoxidase-deficient animals was comparable to that of the wild-type animals.

Levels of free 3-chlorotyrosine and 3-bromotyrosine rise markedly during sepsis. To determine whether products of the myeloperoxidase system accumulate during sepsis, attention was directed to 3-chlorotyrosine, a product of cytotoxic HOCl (ref. 28). To explore the physiological significance of bromination by myeloperoxidase, levels of 3-bromotyrosine were also quantified. To recover free 3-chlorotyrosine and 3-bromotyrosine in the cellular and extracellular components of the lavage fluid, wild-type mice were subjected to CLP. After 24 hours, inflammatory fluid was harvested from the peritoneum by lavage. The lavage fluid, which contained white blood cells, bacteria and inflammatory exudate, was frozen. To recover free amino acids, thawed fluid was centrifuged to pellet cellular debris and the supernatant was harvested.

Amino acids were derivatized with ethyl heptafluorobutyrate and MtBSTFA and analyzed by GC/MS in the EC-NCI mode. To prevent the generation of halogenated tyrosines during sample preparation (ref. 24), a highly sensitive (<100 amol) and specific GC/MS method that avoids acidic conditions was used. (refs. 24, 25).

Figure 2:
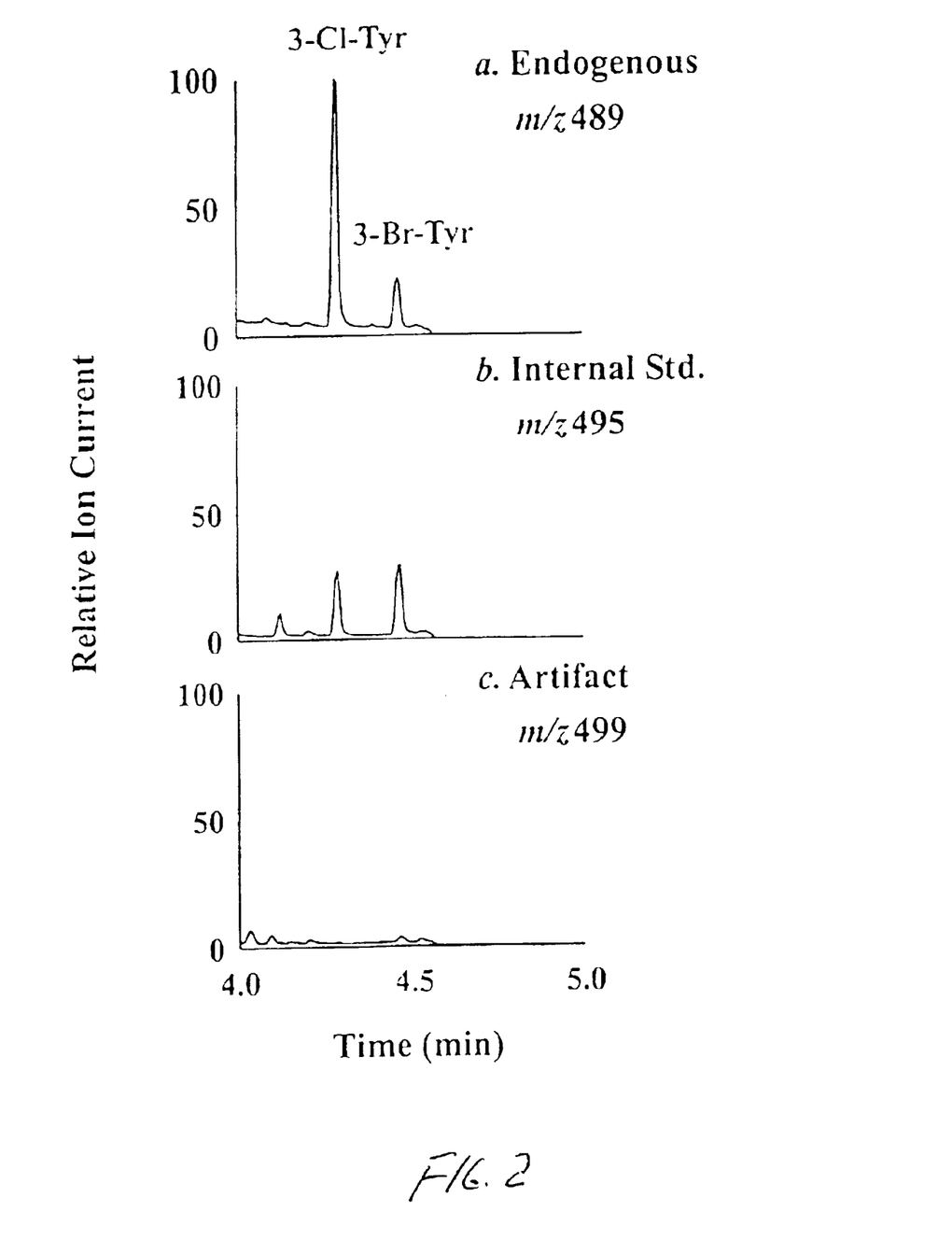
FIG. 2 shows EC-NCI GC/MS analysis of the ethyl heptafluorobutyrate, MtBSTFA derivatives of 3-bromotyrosine and 3-chlorotyrosine in peritoneal inflammatory fluid of a wild-type mouse subjected to CLP. Note the simultaneous monitoring of A, endogenous (m/z 489), B, isotope-labeled (m/z 495), and C, artifactual (m/z 499) 3-chlorotyrosine (3-Cl-Tyr) and 3-bromotyrosine (3-Br-Tyr).

The procedure detected compounds that exhibited major ions and retention times identical to those of authentic 3-chlorotyrosine and 3-bromotyrosine (FIG. 2a). Selected ion monitoring showed that the ions derived from the amino acids co-eluted with those derived from $^{13}$C-labeled internal standards (FIG. 2a,b). The identity of each compound was confirmed by comparison with authentic standards, using MtBSTFA derivatives of each oxidized amino acid. To monitor any artifactual generation of halogenated amino acids, L-[$^{13}$C$_9$, $^{15}$N]tyrosine was included in the samples and observation was made for L-3-chloro[$^{13}$C$_9$, $^{15}$N]tyrosine or L-3-bromo[$^{13}$C$_9$, $^{15}$N]tyrosine (FIG. 2c). Artifact formation was negligible when either biological material or pure tyrosine was analyzed with this method.

Figure 3A:
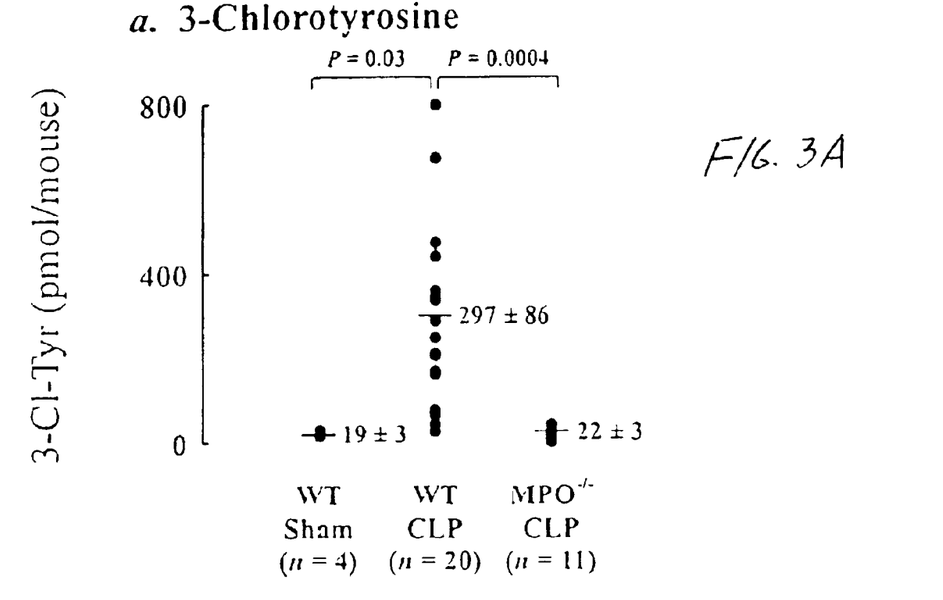
Figure 3B:
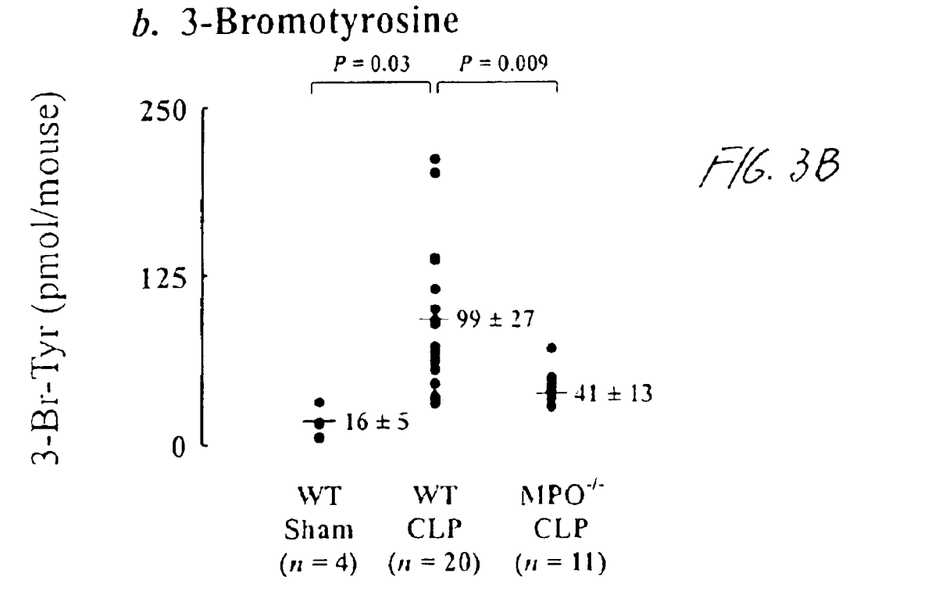

Peritoneal fluid from the sham-operated animals contained only low levels of 3-chlorotyrosine and 3-bromotyrosine (FIG. 3a,b). Fluid from the CLP animals contained 16-fold higher levels of 3-chlorotyrosine (P=0.03) and 6-fold higher levels of 3-bromotyrosine (P=0.03). These observations indicate that generation of halogenating intermediates increases dramatically during acute inflammation induced by sepsis.

Myeloperoxidase generates 3-chlorotyrosine and 3-bromotyrosine during sepsis. To determine whether a pathway involving myeloperoxidase is responsible for the elevated levels of halogenated L-tyrosines seen in inflammatory exudates, levels of the amino acids in septic myeloperoxidase-deficient mice were quantified. Whereas lavage fluid levels of free 3-chlorotyrosine and 3-bromotyrosine rose when the wild-type mice became septic, 3-chlorotyrosine levels barely increased after the myeloperoxidase-deficient animals were subjected to CLP (P=0.0004). The genetically altered mice also produced 59% less 3-bromotyrosine after CLP than the wild-type mice (P=0.009).

The myeloperoxidase-deficient animals used for these experiments had been backcrossed at least 4 generations into the C57Bl/6J background. To ensure that variability in the animals' genetic background had no bearing on the results, CLP was performed on two groups of wild-type mice that represented the two backgrounds of the myeloperoxidase-deficient mice. The C57Bl/6J (n=11) and Sv129/J (n=9) wild-type animals displayed similar patterns of tyrosine chlorination and bromination.

Myeloperoxidase was undetectable when peritoneal cells (predominantly macrophages) isolated from the sham-operated animals were immunoblotted. Peritoneal cells from wild-type mice subjected to CLP had markedly higher levels of immunoreactive myeloperoxidase, as would be expected for an acute neutrophilic inflammatory response. In contrast, peritoneal cells isolated from the septic myeloperoxidase-deficient mice contained no immunoreactive protein. These results indicate that the number of myeloperoxidase-containing cells increases markedly in the normal mouse peritoneum during sepsis and that myeloperoxidase-deficient mice lack immunoreactive enzyme.

The decreased ability of myeloperoxidase-deficient animals to generate 3-bromotyrosine suggested that myeloperoxidase produces brominating intermediates in vivo. Alternatively, the genetic manipulation might have deleted eosinophil peroxidase as well as myeloperoxidase. In humans, the gene for this brominating enzyme lies near the myeloperoxidase gene, on chromosome 17 (ref. 29). To exclude the possibility of a double deletion, peroxidase activity was measured in inflammatory cells isolated from wild-type and myeloperoxidase-deficient mice were subjected to CLP. The wild-type cells generated a single major band of material with peroxidase activity that co-migrated with human myeloperoxidase. This material was undetectable in cells isolated from myeloperoxidase-deficient CLP-treated mice. Thus, the peroxidase in the inflammatory cells that appears in the peritoneum after CLP is myeloperoxidase rather than eosinophil peroxidase.

In contrast, extracts of white blood cells isolated from the peritoneal cavity of wild-type mice injected with thioglycollate produced two bands of peroxidase activity on nondenaturating polyacrylamide gel electrophoresis. The rapidly and slowly migrating bands co-migrated with human eosinophil peroxidase and human myeloperoxidase, respectively. Cell extracts from the myeloperoxidase-deficient mice produced only the rapidly migrating band that corresponded to eosinophil peroxidase. These results suggest that both the wild-type mice and the genetically altered mice were able to make eosinophil peroxidase. Collectively, these observations strongly suggest that myeloperoxidase was the enzyme that generated 3-chorotyrosine and 3-bromotyrosine in septic wild-type mice subjected to CLP.

Physiological concentrations of $Br^-$ modulate the bactericidal activity of myeloperoxidase in vitro. Having shown that mice without myeloperoxidase are more vulnerable to sepsis than wild-type mice and also generate much lower levels of halogenated tyrosines, attention was focused directly at the effects of halides and myeloperoxidase on a bacterial pathogen, *Klebsiella pneumoniae*. The complete myeloperoxidase-$H_2O_2$—$Cl^-$ system, as described above, killed 47% of the bacteria in the incubation mixture. Adding a low concentration (1 $\mu$M) of Br markedly increased bacteria killing (72% dead); higher concentrations (10 $\mu$M) of $Br^-$ were completely inhibitory. Therefore, physiologically plausible variations in [$Br^-$] markedly affect the ability of myeloperoxidase to kill *K. pneumoniae* in vitro.

Myeloperoxidase brominates tyrosine in vitro. Exploration was made for possible mechanisms of this cytotoxic effect of bromide by determining whether the transhalogen pathway that brominates nucleosides and nucleobases (ref. 12) can also halogenate tyrosine, which was brominated in the CLP experiments. For these experiments, N-acetyl-L-tyrosine was used rather than L-tyrosine itself to avoid chloramine formation and to prevent the conversion of L-tyrosine to p-hydroxyphenylacetaldehyde (ref. 22).

Figure 4:
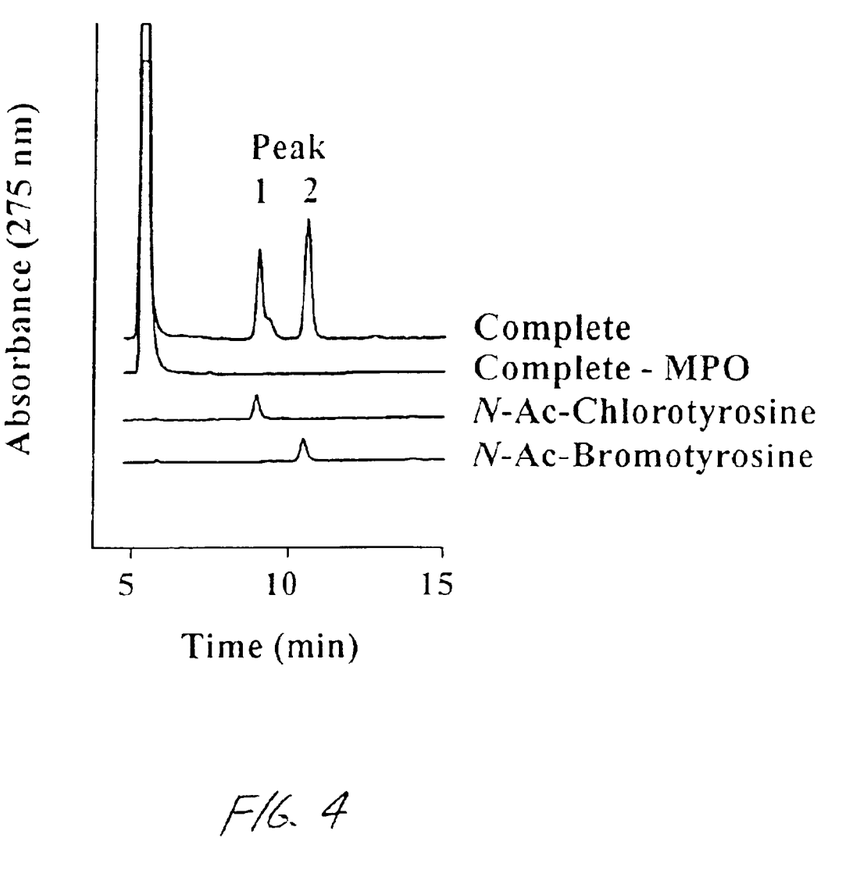
FIG. 4 shows reverse-phase HPLC analysis of N-acetyl-L-tyrosine (N-Ac-tyrosine) exposed to the myeloperoxidase-$H_2O_2$—$Cl^-$—$Br^-$ system. Reactions proceeded for 60 min at 37° C. in Chelex-treated buffer A (100 mM NaCl, 50 mM sodium phosphate, 100 $\mu$M DTPA, pH 4.5) supplemented with 3 nM myeloperoxidase, 1 mM N-Ac-tyrosine, 10 $\mu$M NaBr, and 50 $\mu$M $H_2O_2$. The reactions were initiated with $H_2O_2$ and terminated with 0.1 mM methionine.

After exposure of N-acetyl-L-tyrosine to enzyme, $H_2O_2$, and plasma concentrations of halide (100 mM $Cl^-$ and 10 $\mu$M $Br^-$), reverse-phase HPLC detected early and late eluting products that respectively co-migrated with authentic N-acetyl-L-3-chlorotyrosine and N-acetyl-L-3-bromotyrosine (FIG. 4). Negative-ion electrospray ionization tandem mass spectrometry confirmed the identities of the halogenated amino acids.

Figure 5A:
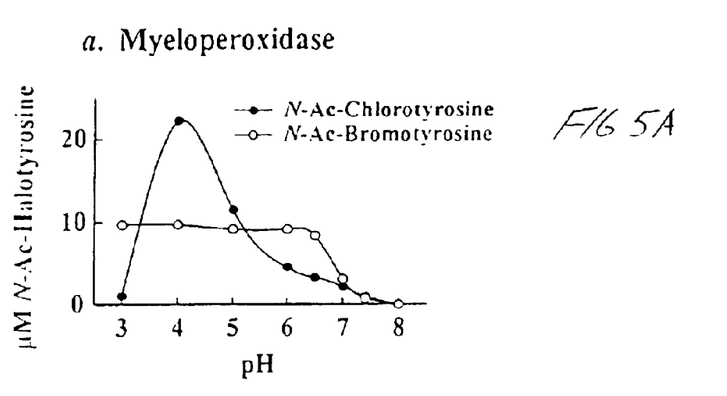
Figure 5B:
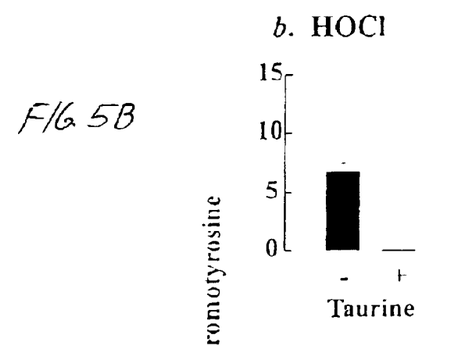

Both chlorination and bromination of N-acetyl-L-tyrosine were optimal under acidic conditions, but significant levels of the halogenated amino acids were also generated at neutral pH (FIG. 5a). Under acidic (pH 5.9) and neutral conditions, bromination by myeloperoxidase required both enzyme and $H_2O_2$; it was inhibited by catalase (a peroxide scavenger), sodium azide (a heme poison), and taurine (a scavenger of hypohalous acids).

Figure 6A:
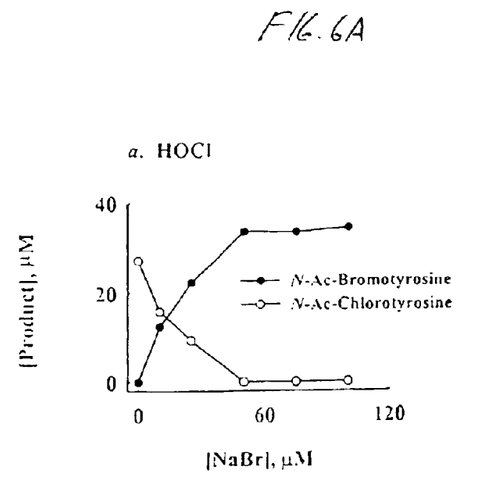
Figure 6B:
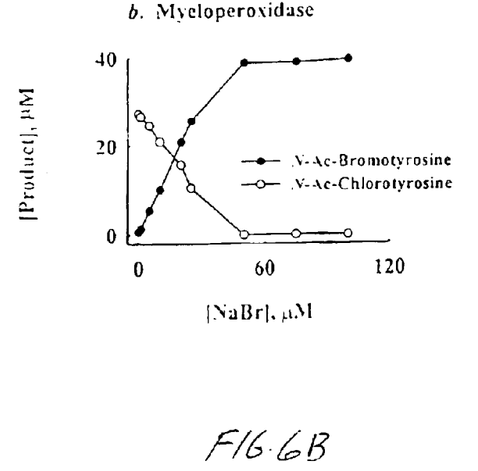

Myeloperoxidase brominates N-acetyl-L-tyrosine at physiologically plausible concentrations of halide ion. It was next determined whether myeloperoxidase prefers to use bromide or chloride when it oxidizes tyrosine under physiological conditions. In the presence of 100 mM $Cl^-$ alone, N-acetyl-L-3-chlorotyrosine was the principal product when either reagent HOCl or the myeloperoxidase-$H_2O_2$ system oxidized N-acetyl-L-tyrosine under acidic (FIG. 6a,b) or neutral conditions. Adding 1M levels of $Br^-$ (in the presence of 100 mM $Cl^-$) to either oxidation system generated N-acetyl-L-3-bromotyrosine and caused a corresponding decrease in N-acetyl-L-3-chlorotyrosine production (FIG. 5a, FIG. 6a,b). The relative yields of N-acetyl-L-3-bromotyrosine and N-acetyl-L-3-chlorotyrosine depended on the pH and [$Br^-$] in the reaction mixture (FIG. 5a; FIG. 6a,b).

Figure 6C:
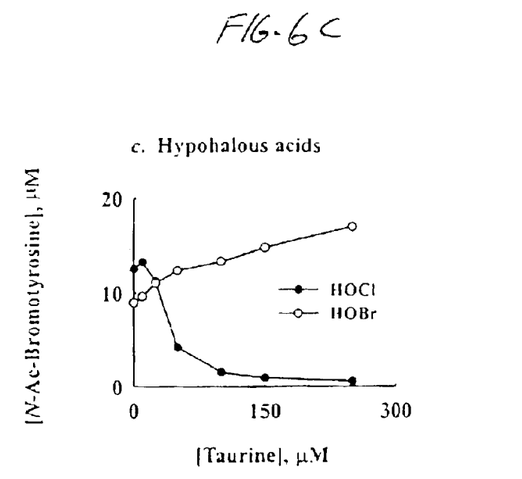
Figure 6D:
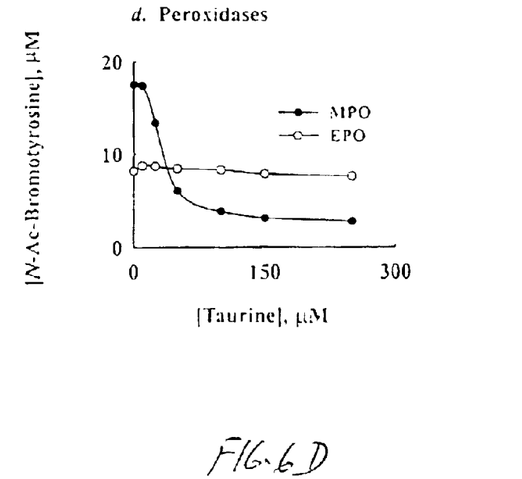

Under mildly acidic conditions (pH 5.9), taurine—a scavenger of HOCl—inhibited the formation of N-acetyl-L-3-bromotyrosine by the HOCl-$Cl^-$—$Br^-$ system (FIG. 6c). In striking contrast, it stimulated N-acetyl-L-3-bromotyrosine formation by hypobromous acid (HOBr), suggesting that bromamines are potent brominating agents. Taurine also inhibited L-tyrosine bromination by the myeloperoxidase-$H_2O_2$—$Cl^-$—$Br^-$ system (FIG. 6d). However, it failed to affect production of N-acetyl-L-3-bromotyrosine by the eosinophil peroxidase-$H_2O_2$—$Cl^-$—$Br^-$ system (FIG. 6d). These observations strongly imply that myeloperoxidase first oxidizes $Cl^-$ to HOCl and that HOCl then reacts with $Br^-$ to generate reactive brominating intermediates.

Figure 5C:
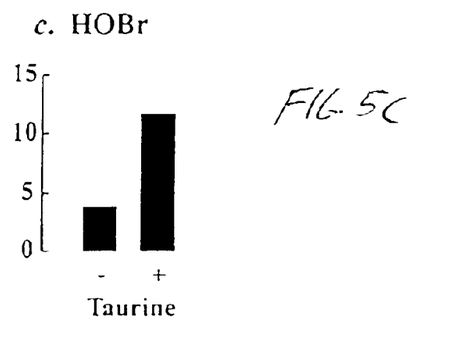
Figure 5D:
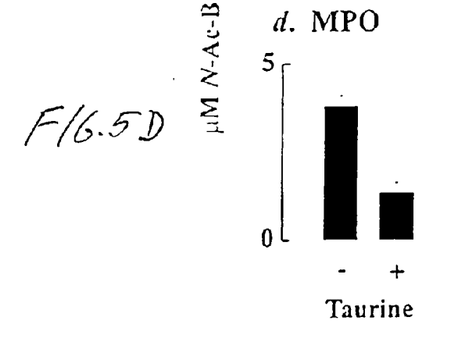
Figure 5E:
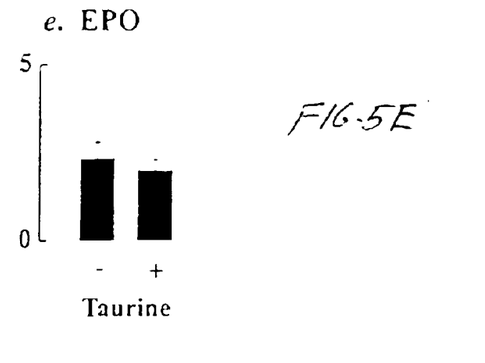

Under neutral conditions, taurine completely inhibited the formation of N-acetyl-L-3-bromotyrosine by the HOCl—$Cl^-$—$Br^-$ system but only partially inhibited the myeloperoxidase-$H_2O_2$—$Cl^-$—$Br^-$ system (FIG. 5c,d). In contrast, it stimulated N-acetyl-L-3-bromotyrosine formation by HOBr and had little affect on the eosinophil peroxidase-$H_2O_2$—$Cl^-$—$Br^-$ system (FIG. 5c,d). These results suggest that myeloperoxidase oxidizes $Br^-$ by two different pathways. In the pathway that operates under mildly acidic and neutral conditions, the enzyme initially generates HOCl, which then oxidizes $Br^-$. In the pathway that operates only at neutral pH, myeloperoxidase directly oxidizes Br.

Although the inventor is not bound by theory, it is believed that the foregoing results can be explained as follows:

More than 30 years ago, Klebanoff proposed that halogenating intermediates generated by myeloperoxidase are of major importance in killing bacteria (ref. 30). However, the enzyme's role in host defense against invading pathogens has remained unclear. The EXAMPLES herein revealed that myeloperoxidase-deficient mice were more likely than wild-type mice to die after CLP, a clinically relevant model of sepsis that releases bacteria into the peritoneum. This observation supports the understanding that myeloperoxidase generates bacterial cytotoxins in vivo. Moreover, the enzyme was able to use halides to kill *K. pneumoniae* in vitro. It has also been discovered that myeloperoxidase-deficient mice are more likely than wild-type mice to die after *K. pneumoniae* is injected into the peritoneum. Thus, myeloperoxidase appears critical to antibacterial defense mechanisms in mice.

Further evidence that myeloperoxidase contributes to antibacterial defense in vivo came from the observation that levels of 3-chorotyrosine, one of the enzyme's characteristic products, rise markedly in peritoneal lavage fluid after wild-type mice are subjected to CLP. Levels of 3-bromotyrosine were also increased. Septic mice that were deficient in myeloperoxidase failed to generate 3-chlorotyrosine at levels above those observed in sham-operated animals, indicating that myeloperoxidase is the major source of chlorinating oxidants in this sepsis model.

3-Bromotyrosine levels were also markedly lower in the septic myeloperoxidase-deficient animals, though they were slightly higher than in non-septic wild-type mice, presumably because of eosinophil peroxidase activity. These observations indicate that myeloperoxidase generates chlorinating and brominating oxidants, whose production was previously ascribed solely to eosinophil peroxidase (refs. 11, 31, 32). Thus, both myeloperoxidase-dependent chlorination and myeloperoxidase-dependent bromination may represent physiologically relevant pathways for bacterial killing. Hypothiocyanite and other oxidants derived from thiocyante may also play a role because this pseudohalide is present at high concentrations in extracellular fluids and is readily oxidized by peroxidases (ref. 33).

The halogenated intermediates produced by myeloperoxidase include HOCl (refs. 3, 4), a potent cytotoxic oxidant that converts tyrosine to 3-chlorotyrosine. The observations indicate that myeloperoxidase will also brominate tyrosine in vitro at plasma concentrations of halide ions. Remarkably, the bromination pathway operates when $Cl^-$ concentrations are 1,000-fold to 10,000-fold higher than $Br^-$ concentrations. Therefore, it is believed to be physiologically relevant.

N-acetyl-bromotyrosine production by myeloperoxidase occurred at neutral pH but was optimal under acidic conditions. In vivo, therefore, myeloperoxidase might halogenate tyrosine extracellularly at neutral pH and also in the phagolysosome (or hypoxic inflamed tissue) under acidic conditions. At acidic pH, taurine almost completely inhibited bromination, suggesting that HOCl is an intermediate in the pathway. In contrast, taurine only partly inhibited N-acetyl-L-bromotyrosine production by myeloperoxidase at neutral pH, suggesting the existence of a bromination pathway not involving HOCl. One possibility for this second pathway is that myeloperoxidase might directly oxidize $Br^-$ to HOBr, as does eosinophil peroxidase (refs. 11, 20). At neutral pH and 10 $\mu$M $Br^-$, myeloperoxidase produced similar concentrations of N-acetyl-L-bromotyrosine and N-acetyl-L-chlorotyrosine, suggesting that the enzyme could produce halogenating intermediates in the extracellular environment. In contrast, Wu et al. found that neutrophils generated protein-bound 3-chlorotyrosine much more effectively than 3-bromotyrosine (ref. 34). One possible explanation for the discrepancy is that Wu et al. studied halogenation of proteins, whereas the present experiments focused on halogenation of free amino acids.

These observations indicate that mice lacking functional myeloperoxidase are more likely to die from polymicrobial sepsis, that in vivo levels of free 3-chorotyrosine and 3-bromotyrosine rise during sepsis, and that production of these halogenated amino acids is markedly reduced when myeloperoxidase is absent. Thus, myeloperoxidase can produce a variety of chlorinating and brominating intermediates that appear capable of defending mice against CLP-induced sepsis. In the enzyme's absence, end products of these intermediates fail to accumulate in peritoneal fluid, and mice become more vulnerable to infection.

Various other examples will be apparent to the person skilled in the art after reading the present disclosure without departing from the spirit and scope of the invention. It is intended that all such other examples be included within the scope of the appended claims. Thus, the presence and level of the 3-chlorotyrosine and 3-bromotyrosine in the sample of body fluid or tissue also can be determined by procedures other than GC/MS as specifically illustrated herein.

For example, the level of these markers can be determined by conventional immunoprecipitation procedures in an immunoassay with polyclonal or monoclonal antibodies to the marker. One- and two-site radioimmunoassay and enzyme immunoassays, e.g., enzyme-linked immunosorbent assay (ELISA) procedures as described by Engvall and Perlmann, *J. Immunol.*, Vol. 109, pp. 129–135 (1972), can be used for determination of the level of the marker. Monoclonal antibodies for use in immunoassay procedures can be prepared by conventional hybridoma methodology as described by Kohler and Milstein, *Nature*, Vol. 256, pp. 495–497 (1975), and *Eur. J. Immunol.*, Vol. 6, pp. 511–519 (1976), and Goding, "Monoclonal Antibodies: Principles and Practice", Academic Press Inc., New York., 1983.

What is claimed is:

1. A method for detecting conditions indicative of sepsis comprising determining the level of 3-chlorotyrosine or 3-bromotyrosine in a sample of body fluid or tissue withdrawn from a patient suspected of having an infection in which a level elevated from the normal level is indicative of early infection or sepsis.

2. The method of claim 1 in which the level of 3-chlorotyrosine or 3-bromotyrosine is determined or monitored prior to and after the treatment of said patient with therapeutic treatment of infection.

3. The method of claim 1 in which the level of 3-chlorotyrosine is determined.

4. The method of claim 2 in which the level of 3-chlorotyrosine is determined.

5. The method of claim 1 in which the level of 3-bromotyrosine is determined.

6. The method of claim 2 in which the level of 3-bromotyrosine is determined.

7. The method of any of claims 1–6 in which the level of 3-chlorotyrosine or 3-bromotyrosine is determined by gas chromatography and mass spectrometry.

* * * * *

SEQUENCE LISTING

```
<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: /note: "synthetic construct"

<400> SEQUENCE: 1

Asn Thr Leu Pro Lys Leu Asn Leu Thr Ser Trp Lys Glu Thr
1               5                   10
```